US00RE49557E

(19) United States
(12) Reissued Patent
Cully et al.

(10) Patent Number: US RE49,557 E
(45) Date of Reissued Patent: Jun. 20, 2023

(54) METHODS AND APPARATUS FOR AN ADJUSTABLE STIFFNESS CATHETER

(71) Applicant: W. L. Gore & Associates, Inc., Newark, DE (US)

(72) Inventors: Edward H. Cully, Newark, DE (US); Jeffrey B. Duncan, Flagstaff, AZ (US); Benjamin M. Trapp, Phoenix, AZ (US)

(73) Assignee: W. L. Gore & Associates, Inc., Newark, DE (US)

(21) Appl. No.: 16/790,551

(22) Filed: Feb. 13, 2020

Related U.S. Patent Documents

Reissue of:
(64) Patent No.: 9,889,273
Issued: Feb. 13, 2018
Appl. No.: 14/294,008
Filed: Jun. 2, 2014

U.S. Applications:
(63) Continuation of application No. 13/326,093, filed on Dec. 14, 2011, now abandoned.
(Continued)

(51) Int. Cl.
*A61M 25/00* (2006.01)
*A61M 25/01* (2006.01)

(52) U.S. Cl.
CPC ..... *A61M 25/0053* (2013.01); *A61M 25/005* (2013.01); *A61M 25/0012* (2013.01);
(Continued)

(58) Field of Classification Search
CPC ..... A61M 25/0053; A61M 25/0012; A61M 25/005; A61M 25/0102; A61M 25/0045;
(Continued)

(56) References Cited

U.S. PATENT DOCUMENTS 2,517,902 A 8/1950 Luebkeman
4,739,768 A 4/1988 Engelson
(Continued)

FOREIGN PATENT DOCUMENTS

CN 1258826 7/2000
CN 101001658 7/2007
(Continued)

OTHER PUBLICATIONS

International Search Report and Written Opinion received for PCT Patent Application No. PCT/US2011/065515, dated Jun. 8, 2012, 28 pages.
(Continued)

*Primary Examiner* — Catherine S Williams

(57) ABSTRACT

Apparatus and methods for an endovascular catheter that can be inserted within tortuous body anatomies and then selectively stiffened and fixed in place. In a particular embodiment, this stiffness is reversible. The stiffness or a comparable mechanical characteristic of the catheter assembly may be adjusted to a relatively low value during insertion (so that it easily navigates a guide wire or the like), and then subsequently adjusted to a relatively high value in situ to keep the catheter assembly substantially fixed in place (i.e., during delivery of an interventional device).

51 Claims, 12 Drawing Sheets

Related U.S. Application Data

(60) Provisional application No. 61/430,303, filed on Jan. 6, 2011.

(52) U.S. Cl.
CPC ..... *A61M 25/0102* (2013.01); *A61M 25/0045* (2013.01); *A61M 25/0051* (2013.01); *A61M 25/0054* (2013.01); *A61M 2025/0025* (2013.01); *A61M 2025/0064* (2013.01); *A61M 2205/0266* (2013.01)

(58) Field of Classification Search
CPC ..... A61M 25/0051; A61M 25/0054; A61M 2025/0025; A61M 2025/0064; A61M 2205/0266
See application file for complete search history.

(56) References Cited

U.S. PATENT DOCUMENTS

| | | | | |
|---|---|---|---|---|
| 4,962,751 | A | 10/1990 | Krauter | |
| 4,977,887 | A | 12/1990 | Gouda | |
| 5,018,506 | A | 5/1991 | Danna et al. | |
| 5,262,121 | A | 11/1993 | Goodno | |
| 5,337,733 | A | 8/1994 | Bauerfeind et al. | |
| 5,383,852 | A | 1/1995 | Stevens-Wright | |
| 5,482,029 | A | 1/1996 | Sekiguchi et al. | |
| 5,662,621 | A | 9/1997 | Lafontaine | |
| 5,772,681 | A * | 6/1998 | Leoni | A61M 25/005 606/192 |
| 5,810,715 | A | 9/1998 | Moriyama | |
| 5,916,147 | A | 6/1999 | Boury | |
| 5,976,074 | A | 11/1999 | Moriyama | |
| 6,123,084 | A | 9/2000 | Jandak et al. | |
| 6,579,261 | B1 | 6/2003 | Kawamura | |
| 6,800,056 | B2 | 10/2004 | Tartaglia et al. | |
| 7,678,117 | B2 | 3/2010 | Hinman et al. | |
| 7,771,411 | B2 | 8/2010 | Smith et al. | |
| 9,889,273 | B2 | 2/2018 | Cully et al. | |
| 2001/0023369 | A1 * | 9/2001 | Chobotov | A61F 2/07 623/1.11 |
| 2001/0049497 | A1 * | 12/2001 | Kalloo | A61B 1/00082 604/164.01 |
| 2002/0082585 | A1 | 6/2002 | Carroll et al. | |
| 2003/0065373 | A1 | 4/2003 | Lovett et al. | |
| 2004/0034383 | A1 | 2/2004 | Belson | |
| 2004/0186378 | A1 | 9/2004 | Gesswein | |
| 2005/0006009 | A1 | 1/2005 | Esashi et al. | |
| 2005/0277876 | A1 | 12/2005 | Hayden | |
| 2006/0025652 | A1 | 2/2006 | Vargas | |
| 2006/0084964 | A1 | 4/2006 | Knudson et al. | |
| 2006/0111614 | A1 | 5/2006 | Saadat et al. | |
| 2006/0211979 | A1 | 9/2006 | Smith et al. | |
| 2006/0264907 | A1 | 11/2006 | Eskridge et al. | |
| 2007/0088367 | A1 | 4/2007 | Von Weymarn-Scharli | |
| 2007/0135803 | A1 | 6/2007 | Belson | |
| 2007/0249999 | A1 | 10/2007 | Sklar et al. | |
| 2007/0270688 | A1 | 11/2007 | Gelbart et al. | |
| 2008/0147046 | A1 | 6/2008 | McDaniel | |
| 2008/0228168 | A1 | 9/2008 | Mittermeyer et al. | |
| 2008/0249436 | A1 | 10/2008 | Darr | |
| 2009/0030282 | A1 * | 1/2009 | Garcia | B25J 18/06 600/146 |
| 2009/0092794 | A1 | 4/2009 | Attila | |
| 2009/0112063 | A1 | 4/2009 | Bakos et al. | |
| 2009/0187163 | A1 | 7/2009 | Uihlein | |
| 2009/0299343 | A1 | 12/2009 | Rogers | |
| 2010/0010437 | A1 | 1/2010 | Miles et al. | |
| 2010/0076451 | A1 | 3/2010 | Zwolinski et al. | |
| 2011/0040282 | A1 * | 2/2011 | Uihlein | A61M 25/0023 604/525 |
| 2011/0184231 | A1 | 7/2011 | Page et al. | |
| 2012/0179097 | A1 | 7/2012 | Cully et al. | |

FOREIGN PATENT DOCUMENTS

| | | | | |
|---|---|---|---|---|
| CN | 101001658 | A | 7/2007 | |
| CN | 101088451 | | 12/2007 | |
| CN | 101088451 | A | 12/2007 | |
| DE | WO 2007/09334 | * | 8/2007 | A61M 25/00 |
| WO | 92/17236 | A1 | 10/1992 | |
| WO | WO 92/17236 | | 10/1992 | |
| WO | 97/24978 | A1 | 7/1997 | |
| WO | WO 97/24978 | | 7/1997 | |
| WO | 99/60267 | A1 | 11/1999 | |
| WO | WO 99/60267 | | 11/1999 | |
| WO | 2005/118045 | A1 | 12/2005 | |
| WO | WO 2005/118045 | | 12/2005 | |
| WO | 2006/113544 | A2 | 10/2006 | |
| WO | WO 2006/113544 | | 10/2006 | |
| WO | 2007/050718 | A1 | 5/2007 | |
| WO | WO 2007/050718 | | 5/2007 | |
| WO | 2007/093394 | A1 | 8/2007 | |
| WO | WO 2007/093394 | | 8/2007 | |
| WO | 2008/054577 | A1 | 5/2008 | |
| WO | WO 2008/054577 | | 5/2008 | |
| WO | 2009/015373 | A1 | 1/2009 | |
| WO | 2009/015374 | A1 | 1/2009 | |
| WO | WO 2009/015373 | | 1/2009 | |

OTHER PUBLICATIONS

Robin Miles, Articulating Catheter Tip for Catheter Guidance (Jun. 9, 2009) <https://ipo.llnl.gov/?q-technologies-pneumatic_steerable_cath . . . > (visited Dec. 30, 2009).

* cited by examiner

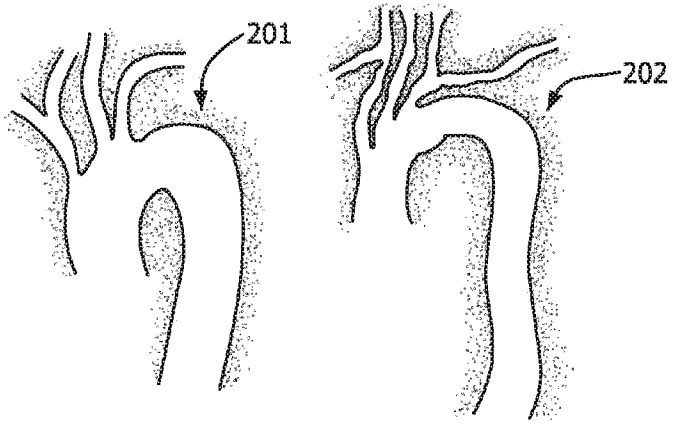
FIG. 2a
FIG. 2b
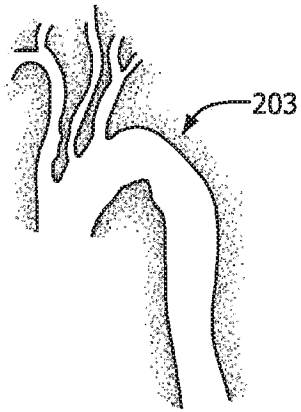
FIG. 2c
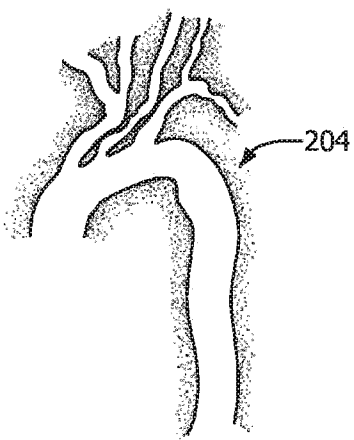
FIG. 2d
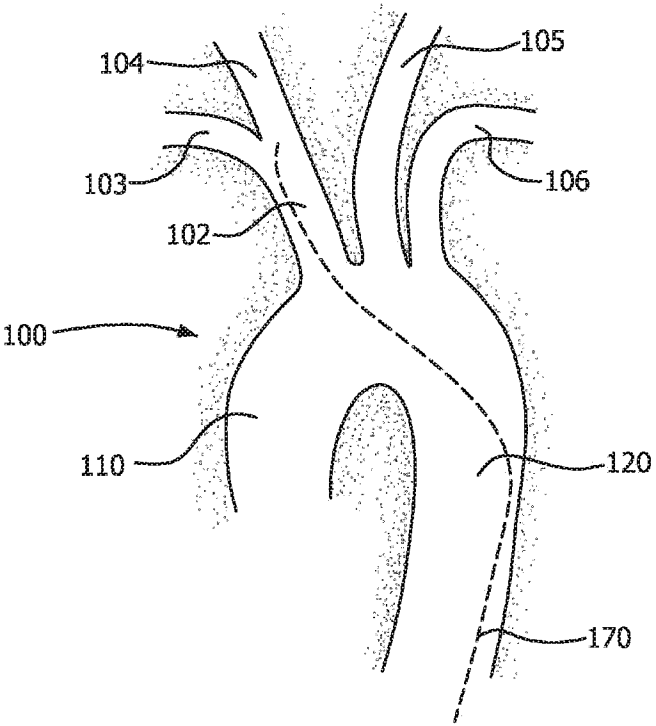
FIG. 1

METHODS AND APPARATUS FOR AN ADJUSTABLE STIFFNESS CATHETER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application *is a reissue application of and claiming priority to U.S. Pat. No. 9,889,273, issued Feb. 13, 2018, which is based on U.S. patent application Ser. No. 14/294,008, filed Jun. 2, 2014, which* is a continuation of U.S. patent application Ser. No. 13/326,093, filed Dec. 14, 2011, which claims the benefit of U.S. Provisional Application No. 61/430,303, filed Jan. 6, 2011, each of which are herein incorporated by reference in their entireties.

TECHNICAL

Embodiments of the subject matter described herein generally relate to catheter systems, and more particularly relate to catheters of the type used in the context of tortuous anatomic features.

BACKGROUND

Catheters are useful in performing a wide range of medical procedures, such as diagnostic heart catheterization, percutaneous transluminal coronary angioplasty, and various endocardial mapping and ablation procedures. It is often difficult, however, to selectively catheterize certain vessels of the human body due to the tortuous paths that the vessels follow. FIG. 1, for example, is a conceptual diagram useful in depicting the human aortic arch 100. As shown, the ascending aorta 110 rises from its origin at the aortic valve (not shown). The right common carotid 104 and the right subclavian 103 branch off of the brachiocephalic artery 102. The left common carotid 105 and the left subclavian artery 106 branch and rise from the aorta just before it turns and descends to the descending aorta 120. Dashed line 170 depicts a typical catheter placement that might be desirable in this context.

Normal aortic arches such as that shown in FIG. 1 rarely require intervention. Instead, interventionalists most often find themselves viewing and navigating diseased and abnormal aortic pathology, such as that shown in FIGS. 2A-2D, which depict assorted variant conditions of the human aortic arch (201-204). It is clear that navigation from the descending aorta 120, up over the arch, and then back to gain access to the right brachiocepalic artery 102 can be extremely difficult in such cases, particularly when the arteries are partially occluded with easily displaced and dislodged build-ups of plaque.

As a result, catheterization procedures often require multiple catheter exchanges—i.e., successively exchanging catheters with different sizes and/or stiffness to "build a rail" through which subsequent catheters can be inserted, eventually resulting in a wire and guide stiff enough to allow delivery of the intended interventional device (e.g., a stent, stent-graft, or the like).

Flexibility is therefore desirable in a catheter to allow it to track over a relatively flexible guidewire without causing the guidewire to pull out. That is, the "navigatibility" of the catheter is important. At the same time, the stiffness or rigidity of the same catheter is desirable to allow the guiding catheter to be robust enough to allow a relatively stiff device (such as a stent) to be tracked through the guiding catheter without causing the guiding catheter to lose position (i.e., becoming "dislodged"). If dislodgement occurs, the entire procedure of guide wire and guide catheter exchanges must be performed again from the beginning.

Often, an optimal balance is sought, such that the distal end of the catheter is flexible, and the proximal end is stiff to enable tracking. However, in order to move the stiff part of a catheter in place, the flexible section typically needs to be buried deep within the anatomy to get "purchase" and to hold position. In many instances, the anatomy does not allow for deep purchase. Accordingly, there is a need for catheter designs and methods that overcome these and other shortcomings of the prior art.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 1 is a conceptual diagram depicting a human aortic arch useful in describing the present invention;

FIGS. 2(a)-(d) depict various common aortic pathologies;

DETAILED DESCRIPTION

Overview

Figure 3:
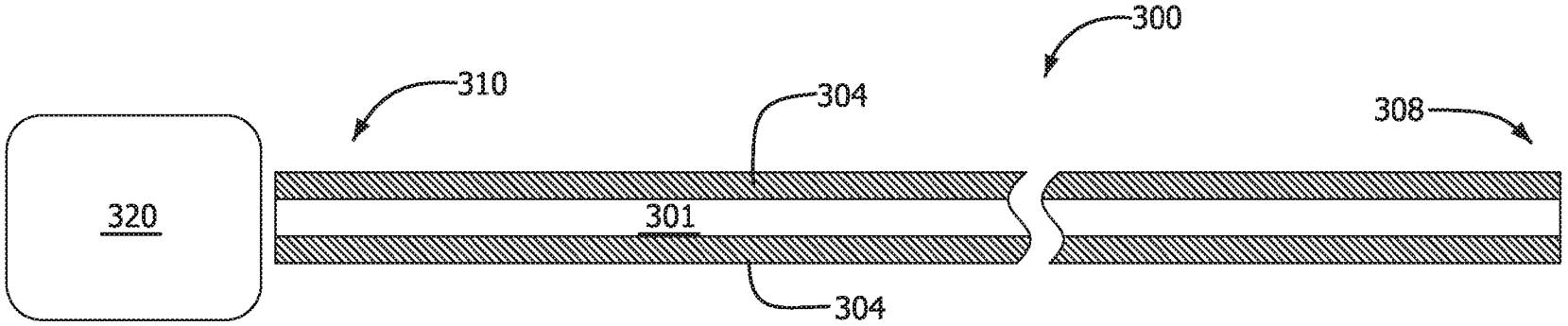
FIG. 3 is a conceptual cross-sectional diagram depicting a catheter apparatus in accordance with one embodiment.

Referring to the longitudinal cross-section shown in FIG. 3, a catheter apparatus (or simply "catheter") 300 in accordance with one embodiment generally includes a generally tubular body (or simply "body") 304 having a delivery lumen (or simply "lumen") 301 defined therein. Catheter 300 extends from a distal end 308 (generally, the end configured to be inserted first within an anatomical feature) and a proximal end 310 opposite distal end 308. A controller 320 communicatively coupled to catheter body 304 and/or lumen 301 will also typically be provided for controlling the operation of catheter 300, as discussed in further detail below.

An activation means (not illustrated in FIG. 3) is provided for causing body 304 to enter two or more states, which may be discrete states or states that vary continuously, or a combination thereof. The activation means will generally include a variety of mechanical, pneumatic, hydraulic, electrical, thermal, chemical, and or other components as described in connection with the various embodiments presented below, and may be incorporated into body 304, lumen 301, controller 320, or a combination thereof. In various embodiments, controller 320 is one component of the activation means.

Figure 19:
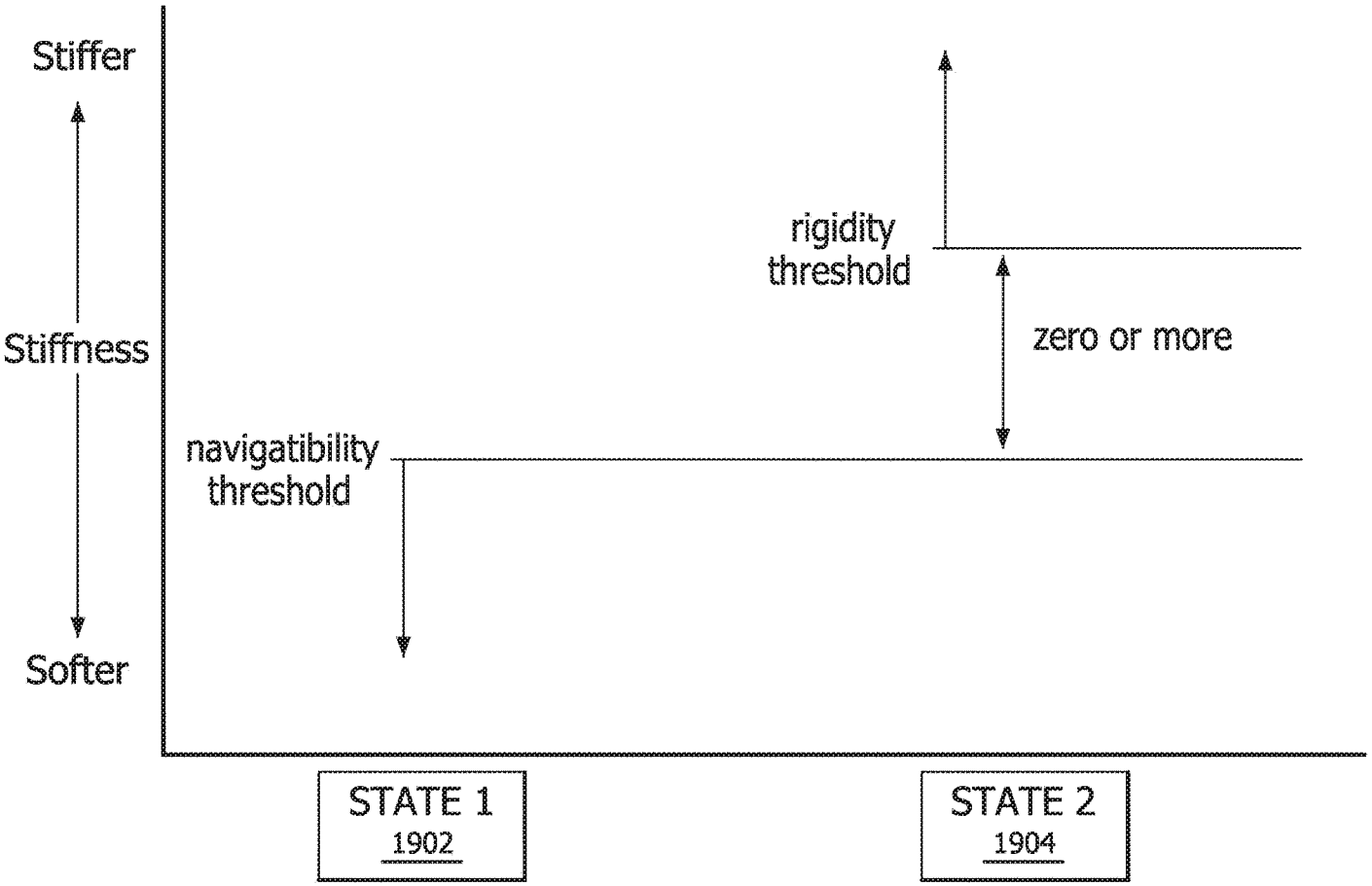
FIG. 19 depicts a qualitative graph showing the value of a stiffness metric in accordance with one embodiment.

In general, body 304 can be selectably placed in at least two states. In the first state, body 304 has a relatively low stiffness and/or has other mechanical properties selected such that catheter 300 can easily be inserted (e.g., via manual axial force applied at proximal end 310) over a guide wire or the like without substantially disturbing the placement of that guide wire. A variety of conventional, commercially available guide wires are known in the art, and need not be discussed in detail herein. In the second state, body 304 has a relatively high stiffness and/or other has mechanical properties selected such that catheter 300 remains substantially in place within the anatomical feature during subsequent operations, including the removal of any guide wire used during insertion. Stated another way, while in the first state, body 304 has a stiffness metric that is equal to or less than a predetermined "navigatibility threshold," and while in the second state, body 304 has a stiffness metric that is greater than or equal to a predetermined "rigidity threshold." This is illustrated in FIG. 19, which qualitatively depicts two states (1902 and 1904) and their corresponding stiffness threshold values (i.e., navigatibility threshold and rigidity threshold, respectively).

The term "stiffness metric" as used herein refers to a dimensionless or dimensional parameter that may be defined in various ways, as described in further detail below. However, regardless of the nature of the stiffness metric, the navigatibility threshold and rigidity threshold define the primary modes of operation of catheter 300. In this regard, note that "stiffness metric" is often used herein to refer to an actual stiffness metric value.

Stiffness Metric and Thresholds

Figure 4:
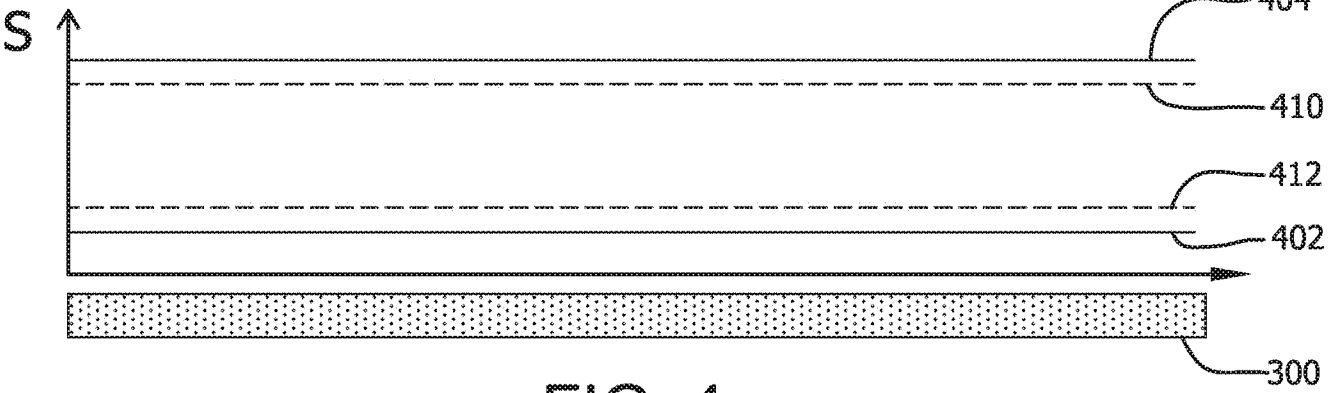
FIGS. 4 and 5 are qualitative graphs showing the value of a stiffness metric as a function of length for catheters in accordance with various embodiments.

FIG. 4 presents a qualitative graphical representation of a stiffness metric (S) as a function of distance along catheter 300 from its proximal end to its distal end. FIG. 4 corresponds to the case where the stiffness metric is substantially uniform along its length, but as will be seen below, the invention is not so limited. Dashed line 412 indicates the navigatibility threshold, and dashed line 410 represents the rigidity threshold for a given stiffness metric. While in the first state (during insertion) catheter 300 has a stiffness metric 402 that is equal to or less than navigatibility threshold 412. Similarly, while in the second state, catheter 300 has a stiffness metric 410 that is greater than or equal to rigidity threshold 410.

In one embodiment, the stiffness metric corresponds to the flexural modulus of catheter 300—i.e., the ratio of stress to strain during bending, as is known in the art. This value may be determined empirically, for example, using a three-point bend test as shown in FIG. 6, wherein catheter 300 (or a portion of catheter 300) is placed on a pair of supports 602 and 604 that are a known distance apart, and a downward (radial) force 608 is applied to catheter 300 via a third structure 606 that is situated between supports 602 and 604.

In another embodiment, the stiffness metric corresponds to an empirical measurement that more closely models the actual operation of catheter 300. For example, FIGS. 7(a)-(c) depict a "dislodgment" test that simulates the placement of a catheter 300 placed at approximately a 90-degree angle (although this angle may vary depending upon the test). More particularly, stationary supports 702, 704, and 706 are positioned in a predetermined geometric relation such that catheter 300 (or a short segment cut from catheter 300) must bend to fit between supports 702 and 704 while contacting support 706. Additional supports (not illustrated) may also be used to assist in placing catheter 300.

Figures 6, 7A, 7B, 7C:
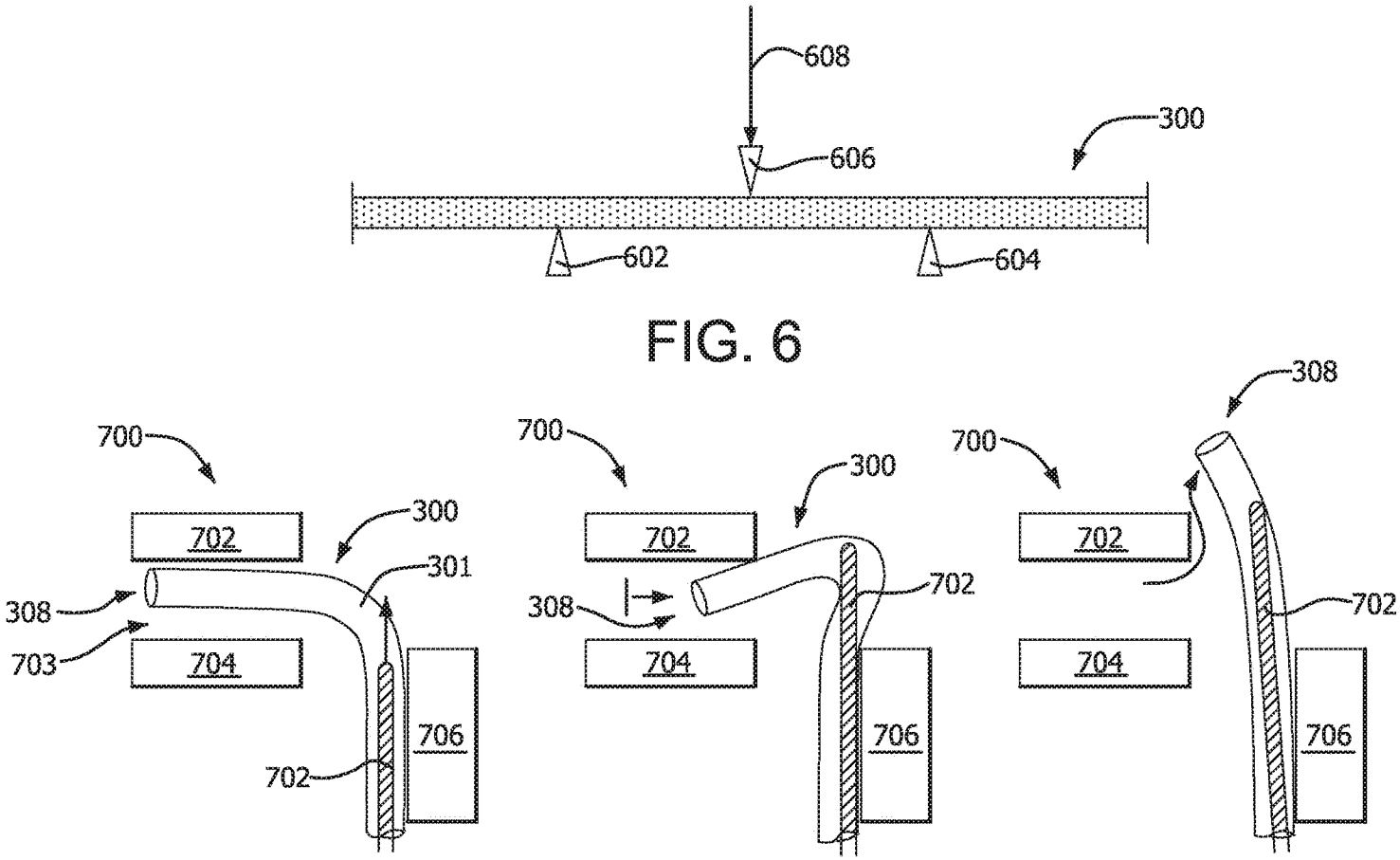
FIG. 6 depicts a three-point bend test used for measuring a stiffness metric.
FIGS. 7(a)-(c) depicts an alternate test used for measuring a stiffness metric.

During the start of the test, a probe 702 is inserted within one end of catheter 300 as shown (FIG. 7(a)). Probe 702 might be configured to approximate the stiffness of a typical stent-graft or the like. As probe 702 is further inserted into the lumen 301 of catheter 300, it makes contact with the inner surface of the lumen 301 and causes end 308 to move with respect to support 702. Ultimately, when probe 702 is inserted with a sufficient force, catheter 300 will be released entirely from between supports 702 and 704 as shown. The force necessary to dislodge catheter 300 in this way then becomes the stiffness metric. The test is advantageously conducted at approximately 37° C. (body temperature). Further, the test may be initiated with an exemplary guide wire in place, thereby allowing the navigatibility threshold to be determined.

Stiffness Metric Variation

Figure 5:
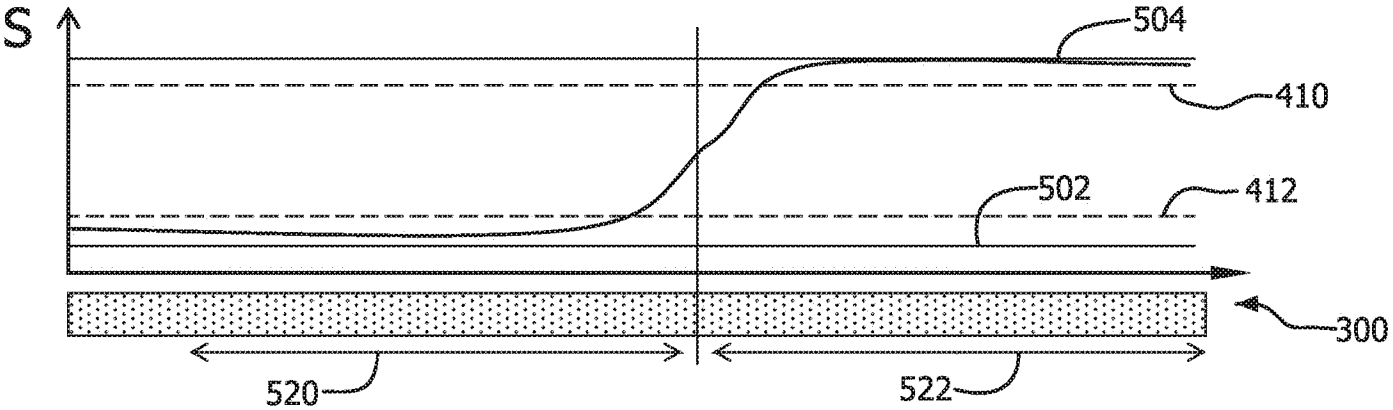

While FIG. 4 depicts the stiffness metric as being invariant over the length of catheter 300, the invention is not so limited. FIG. 5 presents a qualitative graphical representation of stiffness metric (S) as a function of distance along catheter 300 from its proximal end to its distal end; however, in this embodiment, catheter 300 includes two "zones" or segments, each having a corresponding stiffness metric while in the second state. That is, in zone 520, the stiffness metric in the second state (504) is substantially the same as the stiffness metric in the first state (502) (i.e., is generally below the navigatibility threshold 412). Within zone 522, the stiffness metric in the second state (504) is above the rigidity threshold 410.

Catheter 300 may include any number of such zones. Furthermore, the stiffness metric within each zone may be constant or vary continuously. In a particular embodiment, a first zone is adjacent to the distal end of catheter 300, and a second zone is adjacent to the first zone, wherein the stiffness metric of the first zone is less than the stiffness metric of the second zone while in the second state.

In an alternate embodiment, catheter 300 has one stiffness metric value along a first curvature axis and another stiffness metric value along a second curvature axis that is orthogonal to the first curvature axis.

Catheter Body

Catheter body 304 may have any suitable structure, and be fabricated using any suitable combination of materials capable of achieving the selectable stiffness metric described above. For example, in one embodiment, catheter body 304 includes a helical (spiral) channel formed within its exterior and/or its interior. The channel effectively weakens body 304 such that the stiffness metric in the first state is lower than it would be if the body 304 were perfectly tubular. In another embodiment, catheter body 304 includes a plurality of ring-shaped channels formed circumferentially therein. In a particular embodiment, the plurality of ring-shaped channels are distributed irregularly along the tubular body. Such an embodiment allows the baseline stiffness metric to vary in a specified way along the length of catheter 300.

Catheter body 304 may comprise a variety of materials. Typical materials used to construct catheters can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Polyurethane (PU), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PET, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Expanded Polytetrafluoroethylene (ePTFE), Polyvinylidene Fluoride (PVDF), Perfluoroalkoxy (PFA). Other commonly known medical grade materials include elastomeric organosilicon polymers, polyether block amide or thermoplastic copolyether (PEBAX), Kevlar, and metals such as stainless steel and nickel/titanium (nitinol) alloys.

The material or materials selected for catheter body 304 may depend upon, for example, the nature of the activation means used to effect a transition from the first state to the second state of operation. Catheter body 304 may be manufactured, for example, using conventional extrusion methods or film-wrapping techniques as described in U.S. Pat. App. No. 2005/0059957, which is hereby incorporated by reference. Additional information regarding the manufacture of catheters may be found, for example, at U.S. Pat. No. 5,324,284, U.S. Pat. No. 3,485,234, and U.S. Pat. No. 3,585,707, all of which are hereby incorporated by reference.

Activation Means (Generally)

Catheter 300 includes activation means for causing body 304 to enter two or more states as detailed above. The activation means may make use of a variety of physical phenomenon and be composed of any number of components provided within and/or communicatively coupled to catheter 300, including for example, controller 320 as illustrated in FIG. 1. The change of state may be accomplished, for example, via mechanical activation, electrical activation, pneumatic activation, chemical activation, and/or thermal activation. Typically, activation will occur subsequent to catheter placement—i.e., in situ. Various specific types of activation means will now be discussed below in conjunction the exemplary embodiments.

Embodiment 1

Thermal Activation

In one embodiment, the activation means includes a controller 320 communicatively coupled to body 304 as well features within body 304 that are together adapted to place the body in the second state by subjecting at least a portion of the catheter 300 to a reduction or change in temperature.

Figure 8A:
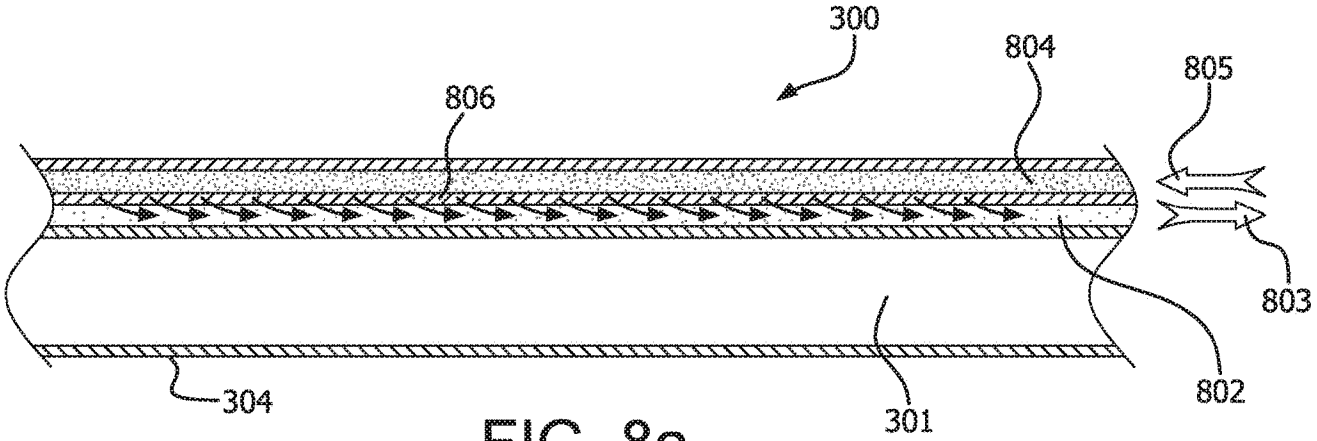
FIGS. 8(a)-(b) depicts a catheter apparatus in accordance with one embodiment.
Figure 8B:
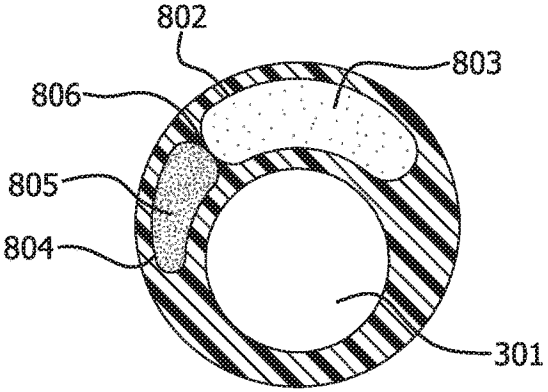

Referring now to FIGS. 8 (a)-(b) in conjunction with FIG. 1, a catheter 300 in accordance with one embodiment generally includes two auxiliary lumens or channels 802 and 804 that are interconnected (e.g., fluidly coupled near a distal end) such that the coolant travels through body 304. The channels 804 and 802 are separated, for example, by a membrane (such as an ePTFE membrane) 806.

After delivery of catheter 300 (during which it is in the first state), a coolant 805 such as liquid nitrogen is supplied to channel 804 (e.g., via a coolant delivery system within controller 320), where it travels parallel to lumen 301 along the length of (or a portion of) body 304. As the changes from liquid to gas at membrane 806, it cools body 304 as well as membrane 806. The materials for catheter body 304 and/or membrane 806 are selected that their stiffness increases as the temperature is reduced. Exemplary materials include, for example, urethane and the like. As channel 804 is significantly smaller than channel 802, compressed gas 803 is allowed to expand as it passes through membrane 806 into channel 802.

As a result of heat transfer from the coolant, the coolant (in the case of liquid nitrogen) changes to a gas phase and exits through channel 802. In other embodiments, the coolant remains in liquid form during operation. Suitable coolants include, for example, chilled saline, liquid $CO_2$, liquid $N_2$, and the like. Other approved medical chilling methods may also be employed.

Embodiment 2

Axial Compression

Figure 16:
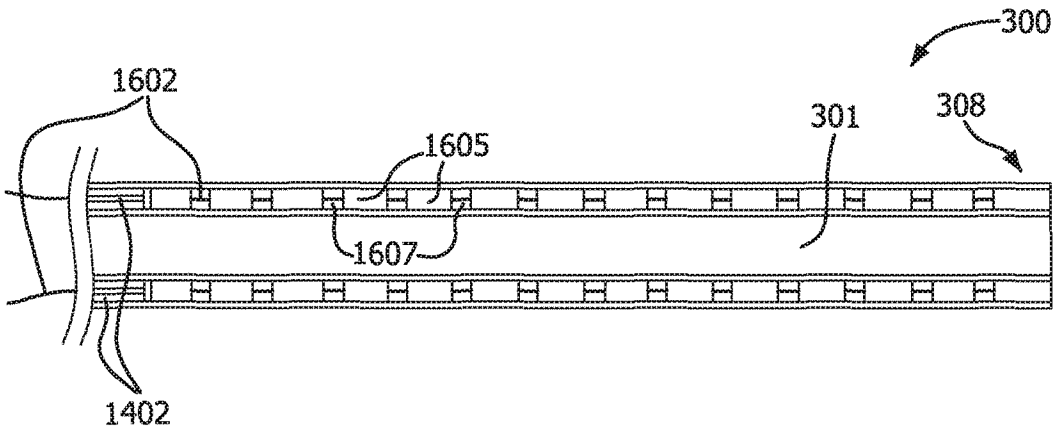
FIGS. 16-17 depict a catheter apparatus in accordance with one embodiment.
Figure 17:
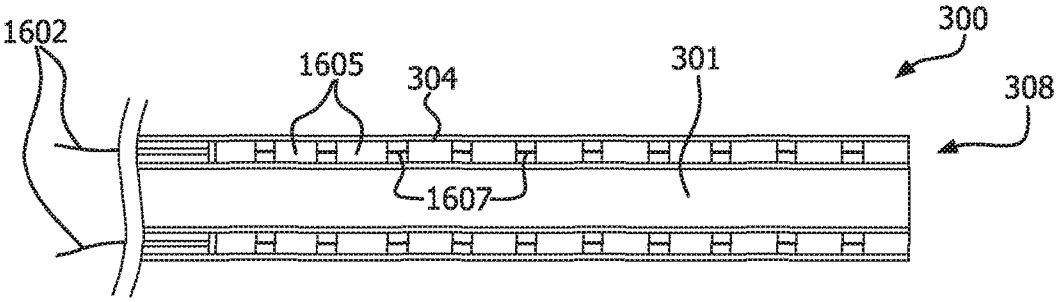

Referring now to FIGS. 16 and 17 in conjunction with FIG. 1, in one embodiment, the activation means includes controller 320 communicatively coupled to the body 304 and components within body 304 that are adapted to place body 304 in the second state by subjecting it to an increase in axial compression.

As shown in FIG. 16, one or more tension lines 1602 may be used to selectively apply a compressive force to body 304. The tension lines 1602 are attached at the distal end 308 of catheter 300 and are slideably received by corresponding accessory lumens 1402 that pass through a series of body segments 1605. The accessory lumens 1402 are preferably sized to allow the free axial movement of tension lines 1602. Depending upon the particular design, body segments 1605 will typically be separated by a small interstitial gaps 1607.

The tension lines 1602 are subjected to approximately zero tension (i.e., are generally "slack") while navigating the anatomy during the first state; however, when stiffening of all or a portion of catheter 300 is desired, tension lines 1602 are pulled substantially simultaneously as depicted in FIG. 17. Gaps and the orientation between body segments 1605 may be optimized to reduce (and/or increase the repeatability of) the foreshortening that occurs when tension is applied. In one embodiment, tension wires 1602 are attached to a floating gimbal mechanism incorporated into controller 320. Once tension is applied, the compressive force tends to bind the catheter; thereby decreasing it's flexibility in that section. Reduction in the axial length may accompany the application of tension. That is, as illustrated, the interstitial gaps 1607 may be reduced.

The tension lines may be made of any suitably strong and flexible material, such as polymeric or metallic filaments or ribbons. The force necessary to place catheter 300 in the second state may vary depending upon the length, material, and cross-section of tension lines 1602, as well as the structural characteristics of body 304.

Figure 18B:
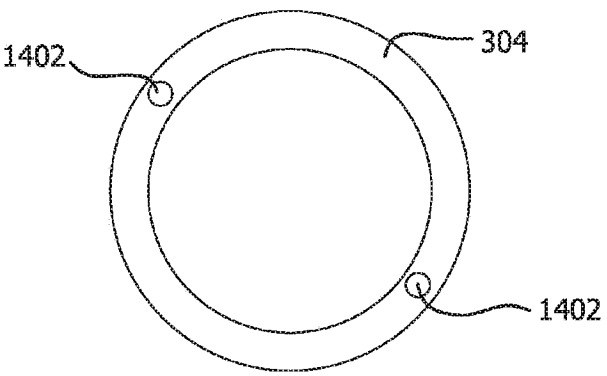
FIGS. 18(a)-(c) depicts lumen configurations in accordance with various embodiments.
Figure 18C:
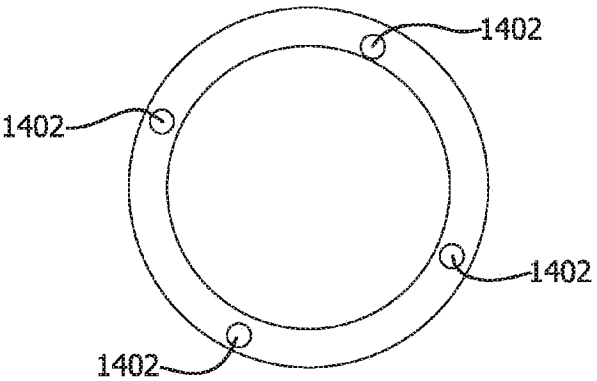
Figure 18A:
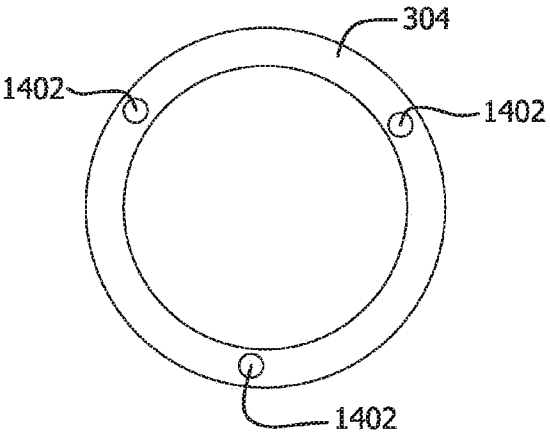

Any number of tension lines 1602 and accessory lumens 1402 may be used. FIGS. 18(a)-(c) present a cross-sectional view of various designs for catheter body 304, including three equidistant accessory lumens 1402 (FIG. 18(a)), two equidistant accessory lumens 1402 (FIG. 18(b)), and four equidistant accessory lumens (FIG. 18(c)). In addition, equidistant accessory lumens may be distributed in any arbitrary fashion, and need not be symmetrical or equidistant as illustrated.

In one embodiment, the column stiffness of body 304 is modified to allow for tracking, then increased to deployment without foreshortening during stiffening.

Embodiment 3

Radial Compression

In one embodiment, the activation means includes controller 320 communicatively coupled to the body 304 and adapted to place the body 304 in the second state by subjecting at least a portion of the tubular body to an increase in radial compression. For example, body 304 may include two fluid impermeable layers defining a pressure-responsive chamber and at least one interstitial structure provided within the pressure-responsive chamber. The controller is configured to cause a change in internal pressure within the pressure-responsive chamber; and the interstitial structure is adapted to exhibit radial compression in response to the change in internal pressure.

Figure 9:
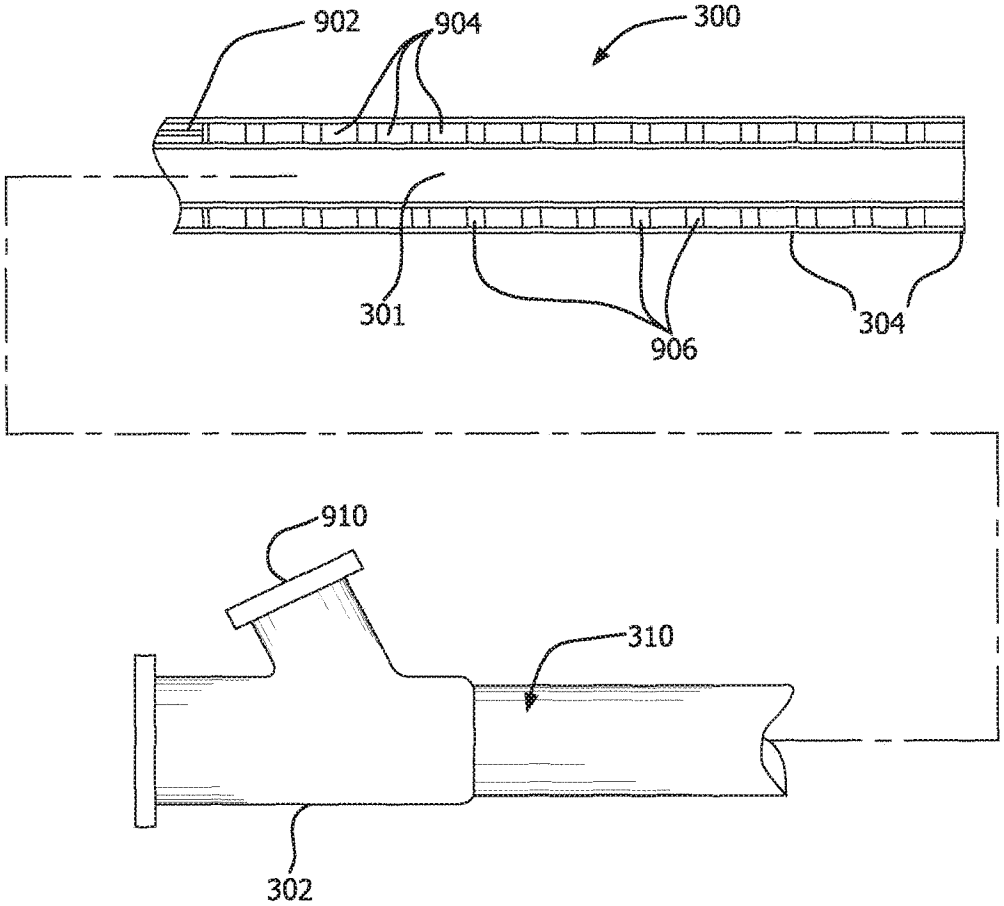
FIG. 9 depicts a catheter apparatus in accordance with one embodiment.
Figure 12:
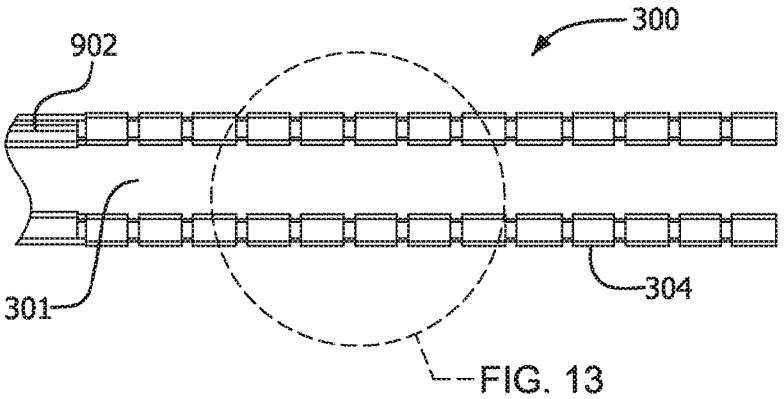
FIGS. 12-13 depict a catheter apparatus in accordance with one embodiment.
Figure 13:
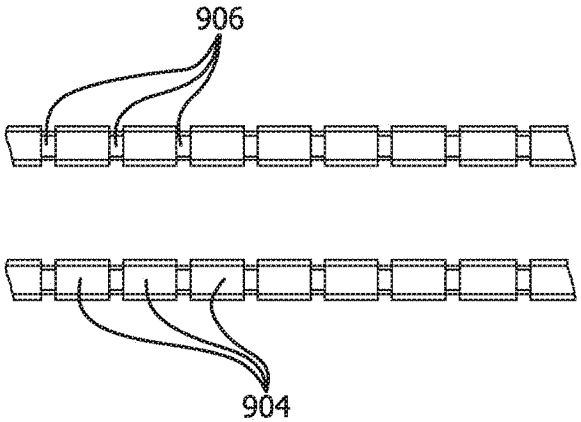

Referring now to FIG. 9, in the illustrated embodiment catheter 300 includes an accessory lumen 902 extending from chambers 906 to a hub 302. Hub 302 in this embodiment is configured as a standard "Y" fitting, wherein negative pressure (i.e., a reduction from some baseline pressure) is applied be attaching a syringe to luer fitting 910. When negative pressure is applied, chambers 906 collapse and apply pressure to corresponding body segments 904 (as illustrated in FIGS. 12 and 13). The pressure is preferably great enough to cause a change in stiffness metric of the affected portion of catheter 300.

Figure 10A:
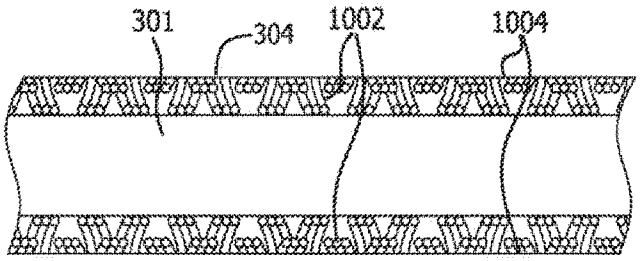
FIGS. 10 (a)-(b) and 11 depict a catheter apparatus in accordance with one embodiment.
Figure 10B:
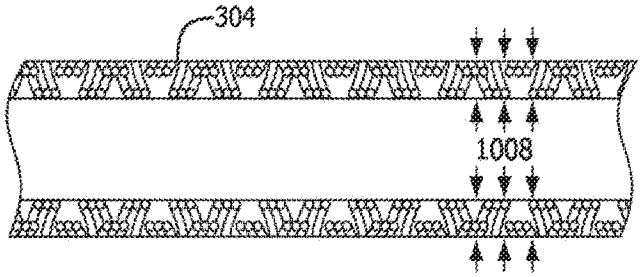

In an alternate embodiment shown in FIGS. 10A and 10B, the body 304 comprises a layered structure 1002 (i.e., an interstitial component) positioned between two or more layers of an air-impermeable chamber 1004. To facilitate the use of negative pressure, the chamber 1004 includes a flexible polymeric material configured to be non-permeable while in the bloodstream. The flexible polymeric comprise, for example, Polyethylene Terephthalate (PET), Polyurethane, Fluorinated Ethylene Propylene (FEP), Nylons or Flouropolymers, including Polytetrafluoroethylene (PTFE) or Expanded Polytetrafluoroethylene (ePTFE), or combinations thereof.

At atmospheric pressure, bending causes the individual components of layers 1002 to slide across each other with minimum friction. When the individual layers are allowed to slide and act individually, the resulting stiffness metric is very low. Upon application of negative pressure, however, a normal (i.e., radial) force 1008 is created within structure 1002 by the collapse of the flexible polymeric material 1004. This normal force is translated through the layers, increasing the layer-to-layer friction and limiting their ability to slide with respect to each other. As a result, the stiffness metric of the structure is increased. In an alternate embodiment, the pressure is increased in an adjacent pressure chamber, thereby causing that chamber to press the adjacent layered structure.

The layered structure 1002 of the present invention may be manufactured using a variety of processes, including, for example, tape wrapping, braiding, serving, coiling, and manual layup. Suitable materials include, include, fibers/yarns (Kelvar, nylon, glass, etc), wires (flat or round, stainless steel, nitinol, alloys, etc), and/or thin slits of film (Polyester, Nylon, Polyimide, Fluoropolymers including PTFE and ePTFE, etc.) In this embodiment, the change in stiffness metric is easily reversed by allowing the chamber pressure to increase (e.g., by relaxation of a syringe attached to luer fitting 910), thereby decreasing the applied normal force.

Figure 11:
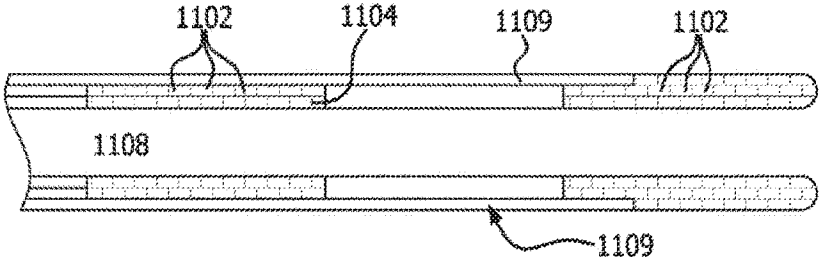

In an alternate embodiment depicted in FIG. 11, multiple discrete air chambers 1102 are distributed along the length of catheter 300 and can be toggled independently. Chambers 1102 may be composed of differentiated layered structures, such as layers of slit, thin film 1104. The distal air chambers may be controlled independently through lumen 1109, while the proximal air chamber is controlled through lumen 1108. This allows the operator to control the segments independently to varying degrees of stiffness change. The lumens 1108 and 1109 may be constructed in a variety of conventional ways, including evacuation through the annular space of the chamber, or individual lumens of tubing such as polyimide that either have an open end in communication with the hub, or holes through the sidewall allowing for unobstructed evacuation.

Embodiment 4

Torsional Activation

In one embodiment, the activation means includes a controller rotatably coupled to at least two body segments (i.e., portions of body 304), wherein controller 320 is configured to apply a relative rotational force between the body segments to cause the tubular body to enter the second state. In one embodiment, two body segments includes an outer layer, an inner layer, and a torsionally-responsive structure provided therebetween. In one embodiment, for example, the torsionally-responsive structure comprises a substantially cylindrical braided structure.

Embodiment 5

Solidifying Material/Membrane

In one embodiment, body 304 includes at least one chamber, a selectably solidifiable material provided within the inner chamber; and a controller fluidly coupled to the at least one inner chamber. The solidifiable material is adapted to substantially solidify in response to, for example, UV radiation, the introduction of a catalyst within the inner chamber, a temperature change, the introduction of water (in the case of hydrophilic particles), acoustic energy (in the case of an acoustically-active polymer), or an electrical current or field (in the case of an electroactive polymer).

Figure 14:
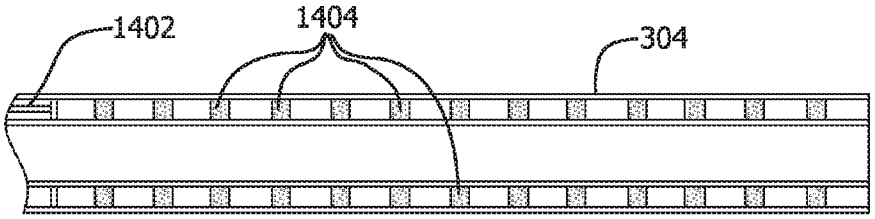
FIGS. 14-15 depict a catheter apparatus in accordance with one embodiment.
Figure 15:
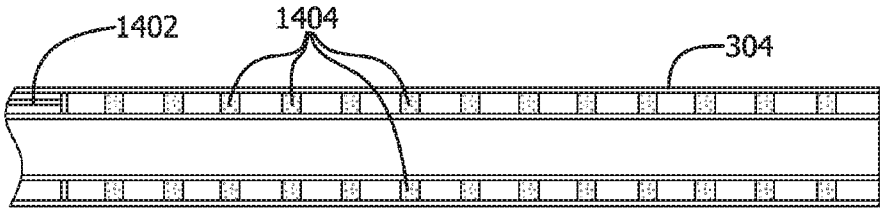

FIGS. 14 and 15 depict an exemplary embodiment incorporating a selectably solidifiable material to effect transition to the second state. As shown in FIG. 14, body 304 is at least partially filled with a medium 1404 (for example, within individual chambers as illustrated) that together can alter the stiffness metric of catheter 300. In this embodiment, the medium 1404 is injected through accessory lumens 1402. Medium 1404 may be a substance that hardens relatively quickly, such as a silicone or polyurethane. If medium 1404 requires a catalyst to activate, that catalyst may already reside within the walls of the body 304 or within the material of catheter 300 itself.

In one embodiment, medium 1404 is a slurry of particles suspended in solution as depicted in FIG. 15. In this case, the walls of body 304 (or membranes provided therein) may be selectively permeable so to allow a carrier liquid to escape (e.g., the chamber and/or catheter body walls) while confining the particles themselves. Once these particles build up and "pack" into the chamber they cause an increased stiffness metric in that section. A variety of suitable particle materials and sizes can be used. In one embodiment, the particle possesses neutral buoyancy in the selected carrier liquid. A hydrophilic particle is advantageous in that it swells during hydration, causing additional binding and increased catheter stiffness.

Embodiment 6

Memory Metal

In one embodiment, the activation means includes at least one metallic structure having shape-memory properties provided within body 304 and communicatively coupled to a power source (e.g. a voltage and/or current source located within controller 320). In one embodiment, the shape-memory metallic structure comprises a Ni/Ti alloy (nitinol).

Conclusion

What has been described are methods and apparatus for an endovascular catheter that can be inserted within tortuous body anatomies and then selectively stiffened and fixed in place. In a particular embodiment, this stiffness is reversible. In this regard, the foregoing detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Thus, although several exemplary embodiments have been presented in the foregoing description, it should be appreciated that a vast number of alternate but equivalent variations exist, and the examples presented herein are not intended to limit the scope, applicability, or configuration of the invention in any way. To the contrary, various changes may be made in the function and arrangement of the various features described herein without departing from the scope of the claims and their legal equivalents.

Techniques and technologies may be described herein in terms of functional and/or logical block components, and with reference to symbolic representations of operations, processing tasks, and functions that may be performed by various computing components or devices.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A catheter apparatus comprising:

a tubular body having a distal end, a proximal end, and a lumen defined therein, the tubular body having a first state, wherein the tubular body has a first value of a stiffness metric, and a second state, wherein the tubular body has a second value of the stiffness metric that is greater than the first value, the tubular body including:

at least two fluid impermeable layers defining a pressure-responsive chamber, and an interstitial structure provided within the pressure-responsive chamber and comprising a plurality of layers including a first cylindrical layer of wrapped tape and a second cylindrical layer of wrapped tape coaxial with the first cylindrical layer of wrapped tape, the first and second cylindrical layers extending along an entire length of the pressure-responsive chamber, the pressure responsive chamber configured to increase radial compression of the plurality of layers in response to negative internal pressure in the pressure-responsive chamber and to decrease radial compression of the plurality of layers in response to non-negative internal pressure in the pressure-responsive chamber, the decrease in radial compression corresponding to a decrease in friction between the plurality of layers along of the interstitial structure and a decrease in the stiffness metric and the increase in radial compression of the plurality of layers of the interstitial structure corresponding to an increase in friction between the plurality of layers of the interstitial structure and an increase in the stiffness metric; and a controller operatively coupled to the tubular body and configured to cause a change in the internal pressure within the pressure-responsive chamber to actuate the tubular body between the first state and second state.

2. The catheter apparatus of claim 1, wherein the plurality of layers of the interstitial structure are configured to be substantially [slideable] *slidable* with respect to each other during the first state, and be substantially non-slidable with respect to each other during the second state.

3. The catheter apparatus of claim 2, wherein the plurality of layers of the interstitial structure each define a substantially cylindrical, helically-wrapped layer.

4. The catheter apparatus of claim 1, wherein the first layer of wrapped tape is a helically-wrapped ePTFE tape layer and the second layer of wrapped tape is a helically-wrapped ePTFE layer.

5. A catheter apparatus comprising:

a tubular body having a distal end, a proximal end, and a lumen defined therein, the tubular body including at least two fluid impermeable layers defining a pressure-responsive chamber and an interstitial structure provided within the pressure-responsive chamber, the interstitial structure comprising a first layer of wrapped tape and a second layer of wrapped tape, the first and second layers of wrapped tape extending along an entire length of the pressure-response chamber; and activation means for selectably causing the tubular body to enter a first state and a second state;

wherein, in the first state, the tubular body has a first value of a stiffness metric that is equal to or less than a predetermined [navigatibility] *navigability* threshold;

wherein, in the second state, the tubular body has a second value of the stiffness metric that is greater than the first value and that is greater than or equal to a predetermined rigidity threshold value; and wherein the activation means includes a controller communicatively coupled to the tubular body and adapted to place the tubular body in the second state by subjecting at least a portion of the tubular body to an increase in radial compression by causing negative pressure within the pressure-responsive chamber thereby causing the collapse of the pressure-responsive chamber.

6. The catheter apparatus of claim 5, wherein the interstitial structure is adapted to exhibit radial compression in response to a change in internal pressure within the pressure responsive chamber caused by the controller.

7. The catheter apparatus of claim 6, wherein the interstitial structure includes a layered structure having a plurality of layers configured to be substantially [slideable] *slidable* with respect to each other during the first state, and be substantially [nonslideable] *non-slidable* with respect to each other during the second state.

8. The catheter apparatus of claim 5, wherein the pressure-responsive chamber is placed under negative pressure in the second state.

9. The catheter apparatus of claim 5, wherein the controller is configured to cause the change of state by pneumatic activation.

10. The catheter apparatus of claim 5, wherein the controller is a syringe.

11. The catheter apparatus of claim 5, further comprising multiple discrete pressure-responsive chambers distributed along a length of catheter, and further wherein the activation means is configured to independently pressurize each of the discrete pressure-responsive chambers.

12. The catheter apparatus of claim 5, wherein the first layer of wrapped tape is a helically-wrapped ePTFE tape layer and the second layer of wrapped tape is a helically-wrapped ePTFE layer.

*13. A catheter comprising:*

*a catheter body having an outer body layer and an inner body layer disposed within the outer body layer to define an air-impermeable chamber there between, at least one of the inner and outer body layers comprising a flexible polymeric material that is at least partially collapsible upon a reduction of an internal pressure of the air-impermeable chamber; and*

*an interstitial component (IC) disposed within the air-impermeable chamber, the interstitial component having at least two opposing portions including a first cylindrical layer and a second cylindrical layer coaxial with the first cylindrical layer and extending along an entire length of the air-impermeable chamber, the at least two opposing portions disposed between the inner and outer body layers and positioned to define a first state where the opposing portions are disposed such that the opposing portions slide across each other with minimal friction and to define a second state where the opposing portions abut each other such that layer-to-layer friction limits the opposing portions to slide with respect to each other, the first state defining a slidable engagement having a first state stiffness metric, the second state defining a non-slidable engagement having a second state stiffness metric,*

*wherein a reversible transition from the first state to the second state is defined by the reduction of the internal pressure driving a collapse of the air-impermeable chamber during which at least one of the inner and outer body layers move towards the other to impart a radial force on the interstitial component, and*

*wherein the reversible transition is further defined by a passive reversal of the collapse of the air-impermeable chamber to at least partially restore the first state during which the inner and outer body layers at least partially move away from each other to reestablish the space between the at least two opposing portions.*

*14. The catheter of claim 13, wherein the first cylindrical layer of the interstitial component has a first surface disposed to face a second surface of the second cylindrical layer of the interstitial component.*

*15. The catheter of claim 13, wherein bending of the body causes the first and second cylindrical layers of the interstitial component to slide across one another in the first state.*

*16. The catheter of claim 13, wherein the first and second cylindrical layers of the interstitial component are configured to radially compress in response to application of the radial force.*

*17. The catheter of claim 16, wherein the radial force increases a stiffness metric of the interstitial component from the first state stiffness metric to the second state stiffness metric.*

*18. The catheter of claim 13, wherein the first and second cylindrical layers of the interstitial component are configured to radially compress in response to application of a negative pressure in the air-impermeable chamber.*

*19. The catheter of claim 18, wherein the first and second cylindrical layers of the interstitial component are configured to exhibit radial compression in response to the negative change in internal pressure in the air-impermeable chamber.*

*20. The catheter of claim 13, wherein the first and second cylindrical layers of the interstitial component are formed by at least one of tape wrapping, braiding, serving, coiling, and manual layup.*

*21. The catheter of claim 13, wherein the inner and outer body layers are configured to move towards one another in response to collapse of the air-impermeable chamber.*

*22. The catheter of claim 13, wherein both of the inner and outer layers forming the air-impermeable chamber are formed of flexible polymer material configured to be non-permeable in a human blood stream.*

*23. The catheter of claim 13, wherein the first state is at a first state pressure approximately equal to atmospheric*

*pressure and the second state is at a second state pressure less than atmospheric pressure.*

*24. A catheter comprising:*

*a catheter body having an outer tubular body and an inner tubular body disposed within the outer tubular body to define a pressure chamber between the inner and outer tubular bodies; and*

*an interstitial structure comprising a first layer and a second layer coaxial with the first layer disposed within the pressure chamber and extending along an entire length of the pressure chamber, the first layer disposed proximate to an inner surface of the outer tubular body and the second layer disposed proximate to an outer surface of the inner tubular body,*

*wherein the catheter comprises a first state defining a first state stiffness metric and a slidable engagement between the first and second layers,*

*wherein the catheter further comprises a second state defining a second state stiffness metric and a non-slidable engagement between the first and second layers,*

*wherein a first transition from the first state stiffness metric to the second state stiffness metric is defined by a collapse of the pressure chamber in response to a reduction in a pressure in the pressure chamber during which at least one of the inner and outer tubular bodies move towards the other, and*

*wherein a second transition from the second state stiffness metric towards the first state stiffness metric is defined by a passive expansion of the pressure chamber during which the inner and outer tubular bodies move away from each other to at least partially reverse the first transition.*

*25. The catheter of claim 24, wherein the first layer and the second layer are configured to slide across each other in the first state and are substantially non-slidable in the second state.*

*26. The catheter of claim 24, wherein bending of the body causes the first layer and the second layer to slide across one another in the first state.*

*27. The catheter of claim 24, wherein the catheter is configured to transition from the first state stiffness metric to the second state stiffness metric in response to application of a radial force.*

*28. The catheter of claim 24, wherein the catheter is configured to transition from the first state stiffness metric to the second state stiffness metric to response to reduction of a pressure.*

*29. A catheter comprising:*

*a catheter body defining a catheter axis and having an outer body layer and an inner body layer disposed within the outer body layer to define a pressure chamber between the inner and outer body layers, at least one of the inner body layer and the outer body layer comprising a flexible polymeric material such that the pressure chamber is configured to collapse upon the application of a reduced pressure within the pressure chamber, the catheter having a first state in which the air chamber is in a non-collapsed orientation prior to the application of the reduced pressure and having a second state in which the air chamber is in a collapsed orientation after the application of the reduced pressure, the inner and outer body layers in the first state each having a smooth surface along an axial length of the respective body layer defining a slidable operation of the catheter in the first state; and*

*an interstitial component including a first component and a second component coaxial with the first component disposed within the air chamber between the inner and outer body layers and extending along the entire length of the air chamber,*

*wherein in the second state at least one of the inner and outer body layers at least in part deforms along the axial length of the respective body layer in response to a normal force defining a rigid non-slidable operation of the catheter in the second state, and*

*wherein in the second state at least one of the first and second components are repositioned by the normal force to permit engagement between the first component and the second component further defining the rigid non-slidable operation of the catheter in the second state.*

*30. The catheter of claim 29, wherein the first and second components are configured to move toward one another to transition between a first state stiffness metric and a second state stiffness metric.*

*31. The catheter of claim 29, wherein the first and second components move towards one another in response to application of a vacuum to the pressure chamber.*

*32. The catheter of claim 29, wherein the interstitial component is configured to transition between a navigable configuration corresponding to the first state and a rigid configuration corresponding to the second state.*

*33. The catheter of claim 32, wherein the interstitial component includes non-axial surfaces in the navigable configuration and axial surfaces in the rigid configuration.*

*34. The catheter of claim 32, wherein the pressure chamber is configured to collapse to result in the body having a first stiffness metric along a first curvature axis and a second stiffness metric along a second curvature axis.*

*35. The catheter of claim 34, wherein the second curvature axis is orthogonal to the first curvature axis.*

*36. The catheter of the claim 35, wherein the inner and outer body layers are configured to move toward one another to result in the body having the first and second stiffness metrics.*

*37. The catheter of claim 36, wherein at least one of inner and outer body layers are configured to warp from an axially aligned state to a non-axially aligned state in response to application of a vacuum to the pressure chamber.*

*38. The catheter of claim 37, wherein the interstitial component includes non-axially aligned surfaces in the navigable configuration and substantially axially aligned surfaces in the rigid configuration and the vacuum is configured to transition the interstitial component between the navigable configuration and the rigid configuration.*

*39. The catheter of claim 37, wherein axial movement between the inner and outer body layers is opposed in the rigid configuration.*

*40. The catheter of claim 39, wherein the inner and outer body layers collapse toward one another to arrest movement between the inner and outer body layers in the rigid configuration.*

*41. The catheter of claim 29, wherein the catheter body includes a plurality of segments defining non-axial surfaces.*

*42. The catheter of claim 29, wherein the catheter body includes two or more zones, and each of the two or more zones include a zone stiffness metric.*

*43. The catheter of claim 42, wherein the zone stiffness metric of each of the two or more zones is variable between the two or more zones.*

*44. A method of increasing a stiffness metric of a catheter from a first state having a flexible orientation to a second state having a comparatively rigid orientation, the method comprising:*

*reducing pressure in a pressure chamber within a catheter body of the catheter to apply an inwardly radial force;*

*advancing a first interstitial component within the pressure chamber towards a second interstitial component within the pressure chamber to engage irregular surfaces of the first and second interstitial components to defining a non-sliding engagement between the first and second components in the second state*

*wherein the first interstitial component and the second interstitial component are coaxial layers that extend along the entire length of the pressure chamber.*

*45. The method of claim 44, wherein advancing the first interstitial component within the pressure chamber towards the second interstitial component includes sliding the first interstitial component relative to the second interstitial component to transition between the first state stiffness metric in the first state and the second state stiffness metric in the second state.*

*46. The method of claim 44, wherein the catheter body includes an outer body layer and an inner body layer to define the pressure chamber, and reducing pressure in the pressure chamber includes applying a vacuum to the pressure chamber to move the outer body layer and the inner body layer toward one another to transition between the first state stiffness metric and the second state stiffness metric.*

*47. The method of claim 46, wherein applying the vacuum to the pressure chamber includes warping at least one of the outer body layer and the inner body layer from an axially aligned state to a non-axially aligned state.*

*48. The method of claim 47, wherein applying the vacuum includes transitioning the body between a navigable configuration corresponding to the first state and a rigid configuration corresponding to the second state.*

*49. The method of claim 48, wherein the catheter body includes non-axially aligned surfaces in the navigable configuration and substantially axially aligned surfaces in the rigid configuration and applying the vacuum to the pressure chamber transitions the layered structured between the navigable configuration and the rigid configuration.*

*50. The method of claim 44, wherein the catheter body includes two or more zones, and each of the two or more zones include a zone stiffness metric and the zone stiffness metric of each of the two or more zones is variable between the two or more zones.*

*51. The method of claim 44, wherein reducing pressure in the pressure chamber includes collapsing the pressure chamber to place the catheter body in the first stiffness metric along a first curvature axis and the second stiffness metric along a second curvature axis that is orthogonal to the first curvature axis.*

* * * * *